United States Patent [19]

France et al.

[11] Patent Number: 5,277,697
[45] Date of Patent: Jan. 11, 1994

[54] PATELLA-FEMORAL BRACE

[75] Inventors: E. Paul France; Lonnie E. Paulos, both of Salt Lake City; Richard L. Ellingson, Draper, all of Utah

[73] Assignee: Hanger Orthopedic Group, Inc., Bethesda, Md.

[21] Appl. No.: 786,187

[22] Filed: Oct. 31, 1991

Related U.S. Application Data

[63] Continuation-in-part of Ser. No. 740,642, Jul. 31, 1991, abandoned, which is a continuation of Ser. No. 568,750, Aug. 17, 1990, abandoned.

[51] Int. Cl.$^5$ .............................................. A61F 5/00
[52] U.S. Cl. ........................................ 602/16; 602/26
[58] Field of Search ...................... 602/5, 28, 16, 26

[56] References Cited

U.S. PATENT DOCUMENTS 1,388,772  8/1921  Sheehan .
1,428,465  9/1922  Willmott .
2,220,836  11/1940  Closson .
2,270,685  1/1942  Miller .

(List continued on next page.)

FOREIGN PATENT DOCUMENTS 0010389    6/1983   European Pat. Off. .
0356623    3/1990   European Pat. Off. .
846895     8/1952   Fed. Rep. of Germany .
2724586   12/1978   Fed. Rep. of Germany .
9017540.9  5/1991   Fed. Rep. of Germany .
840438     4/1939   France .
16032      of 1899  United Kingdom .
2136294A   9/1984   United Kingdom .

OTHER PUBLICATIONS

Palumbo v. Don-Joy, 226 U.S.P.Q. 5–11 (Fed. Cir. 1985).
ASTM, "Standard Test Method for Rubber Property–Durometer Hardness," D:2240-86 (U.S.A., 1986), pp. 227–230.
DONJOY, Inc., "Soft Goods Catalog" (U.S.A., 1988).
DONJOY, Inc., Products Catalog (U.S.A., 1989).
The Physician and Sportsmedicine, "Palumbo Brace" and Pro #180: Dr. 'M' Knee Brace (U.S.A., Sep. 1990), 2 pages.
Cherf, John, "Bracing for Patellar Instability," Clinics in Sports Medicine (U.S.A., Oct. 1990), vol. 9, No. 4, pp. 813–821.

Primary Examiner—Richard J. Apley
Assistant Examiner—Linda C. M. Dvorak
Attorney, Agent, or Firm—Berne S. Broadbent

[57] ABSTRACT

The present invention is directed to a patella-femoral brace which includes an elastic sleeve which is sized so as to be securely positionable about a user's leg and which has a bracing plate located therein which becomes positioned adjacent the lateral side of the patella when the elastic sleeve is correctly positioned about the patient's knee. The brace plate may include a protection pad which extends to cover the lateral side of the knee to protect it from impact or contact with other elements of the knee brace. The brace plate is connected to a set of strap members, each located above and below the patella, and each being capable of wrapping around the medial side of the knee, across the back of the leg, and attaching to a rigid support brace. The support brace includes upper and lower cuffs, each having a single hinge arm which connect together at a hinge. The hinge includes a locking mechanism to prevent hyperextension of the knee. The support brace is fixed in its position on the leg, and the straps are fixed to the cuffs of the support brace, such that the brace plate remains in fixed position relative to the knee to cause a medial pressure to be applied to the patella during flexion and extension thereof for preventing mispositioning (subluxation) of the patella.

8 Claims, 6 Drawing Sheets

U.S. PATENT DOCUMENTS

| | | |
|---|---|---|
| 3,046,981 | 7/1962 | Biggs, Jr. et al. . |
| 3,074,400 | 1/1963 | Schulman . |
| 3,318,305 | 5/1967 | Schultz . |
| 3,387,305 | 6/1968 | Shafer . |
| 3,473,527 | 10/1969 | Spiro . |
| 3,786,804 | 1/1974 | Lewis . |
| 3,804,084 | 4/1974 | Lehman . |
| 3,817,244 | 6/1974 | Taylor . |
| 3,831,467 | 8/1974 | Moore . |
| 3,853,123 | 12/1974 | Moore . |
| 3,926,186 | 12/1974 | Nirschl . |
| 3,945,046 | 3/1976 | Stromgren . |
| 4,064,874 | 12/1977 | Valin . |
| 4,084,584 | 4/1978 | Detty . |
| 4,116,236 | 9/1978 | Albert . |
| 4,201,203 | 5/1980 | Applegate . |
| 4,250,578 | 2/1981 | Barlow . |
| 4,287,885 | 9/1981 | Applegate . |
| 4,296,744 | 10/1981 | Palumbo . |
| 4,370,978 | 2/1983 | Palumbo . |
| 4,423,720 | 1/1984 | Meier et al. . |
| 4,425,912 | 1/1984 | Harper . |
| 4,445,505 | 5/1984 | Labour et al. . |
| 4,607,628 | 8/1986 | Dashefshy . |
| 4,791,916 | 12/1988 | Paez . |
| 4,802,466 | 2/1989 | Meyers et al. . |
| 4,938,207 | 7/1990 | Vargo . |
| 4,941,462 | 7/1990 | Lindberg . |

PATELLA-FEMORAL BRACE

Related Applications

This application is a continuation-in-part of application Ser. No. 07/740,642, filed on Jul. 31, 1991 for PATELLA-FEMORAL BRACE, now abandoned, which is a continuation of our application Ser. No. 07/568,750, filed on Aug. 17, 1990 for PATELLA-FEMORAL BRACE, also abandoned.

BACKGROUND

1. The Field of the Invention

This invention relates generally to a knee support device. More particularly, this invention relates to a device which supports and stabilizes the knee, including the patella, to resist abnormal lateral subluxation of the patella during motion of the knee joint.

2. The Background Art

Anterior knee pain (i.e., pain in the forward part of the knee), is one of the most common complaints that cause patients to consult a knee specialist. A frequent cause of such pain is malalignment of the patellofemoral joint which is often associated with instability of the patella (knee cap).

Patellar instability usually occurs laterally (i.e., in a direction away from the other leg), and is referred to as "patellar subluxation," "patellar dislocation," or "patellar hypermobility." In a patient with this knee disorder, the muscles and ligaments which hold the patella in its proper position in the knee are malaligned, very loose or lax. This condition is caused either by developmental abnormalities (generally in younger children), or by injuries to the muscles and/or ligaments attached to the patella. Because of the very loose placement of the patella in this condition, the patella may become misoriented relative to its normal position during flexion/extension rotation of the knee joint (i.e., during normal "bending" of the leg at the knee joint). Such misorientation usually occurs when the joint is extended under stress, such as during strenuous physical activity in which the knee is carrying an increased load while it is rotating.

Not only can patellar subluxation cause severe pain, the knee is also more prone to give way (buckle) under the strain of a load placed thereon when the patella is not properly oriented. Moreover, continued or frequent abnormal displacements of the patella can cause severe degeneration of the patella and the surrounding knee structure.

The conservative treatment of patellar instability often includes muscle rehabilitation, medication, and/or activity modification. In addition, those skilled in the art have developed numerous types of knee braces to assist in the treatment of patellar instability. Such braces range from very simple to quite complex and have been successful in the treatment of patellar instability to varying degrees.

A simple knee sleeve is often used to provide static patellar support. The sleeve is generally made of an elastic material and has an opening through which the knee cap protrudes. When thus positioned, the sleeve exerts a static force on the knee to assist in maintaining the patella in proper alignment.

Another prior art bracing device comprises an infrapatellar strap. The strap is wrapped around the knee so as to support the patella during motion of the knee joint.

Still another prior art device comprises a bracing pad held in a lateral position with respect to the patella by means of an elastic sleeve and a plurality of elastic straps. This device is intended to apply a medially displacing force to the patella (i.e., a force in a direction toward the other leg), and maintain constant pressure during flexion, extension, and rotation of the knee.

Despite the limited success of some prior art devices in treating patellar instability, the exact function of many of the devices is unclear. For example, some prior art devices may help alleviate pain for a variety of reasons. The warmth the device provides to the knee may be therapeutic. Similarly, sensory feedback may be altered, thereby reducing the patient's awareness of discomfort. Likewise, a possible alteration in circulation is another potential effect of many devices. These nonspecific mechanisms might help explain the potential effectiveness of some prior art patellar bracing devices.

Many existing brace devices are also subject to shifting on the user's knee during movement of the knee joint. Of course, such shifting may cause the brace to become misaligned, thereby significantly reducing the functional effectiveness of the brace.

In addition, the physiology of the knee is such that the patella slips deeply into the cavity provided for it when the knee joint is in hyperextension. In such cases, the structure of existing brace devices is such that the patella may slip below the bracing member and rotate thereunder. The bracing device is thereby rendered largely ineffective.

Further, the mechanical function of existing devices seems limited to applying a medial force to the lateral aspect of the patella in patients with patellar tracking problems. While this function is believed to be based upon sound biomechanical principles, it treats only one cause of patellar instability. There is no known evidence that this function is applicable in treating any other causes. Consequently, there remains a need for a bracing device which more completely enhances and facilitates patellar stability.

BRIEF SUMMARY AND OBJECTS OF THE INVENTION

In view of the foregoing, it is an object of the present invention to provide a bracing device useful for holding and supporting a user's knee during flexion/extension rotational movement thereof.

It is further an object of the present invention to provide a bracing device which is useful for the prevention of patellar subluxation.

It is another object of the present invention to provide a knee brace capable of holding the patella in its proper orientation relative to the remaining knee structure in order to prevent misorientation of the patella during flexion/extension rotational motion of the knee.

Additionally, it is an object of the present invention to provide a knee brace which can fix a bracing member against the patella of the knee in a rigid manner in order to control or prevent lateral movement of the patella relative to the knee joint during flexion/extension rotation and which can also prevent hyperextension of the knee.

It is still another object of the present invention to provide a knee brace as defined above which is simple to attach to a patient, and which will not interfere with a similar brace located on the user's opposite knee.

Consistent with the foregoing objects, and in accordance with the invention as embodied and broadly described herein, a knee brace is disclosed in one embodiment of the present invention as including an elongate annular elastic sleeve member which is sized so as to entirely surround the user's knee and to be held in place by elastic forces. The elastic sleeve member may have formed therein a pocket or other such opening into which a brace plate may be inserted. The brace plate is formed of silicone or other similar semi-rigid, semi-flexible material, and includes a contacting surface which is shaped to conform to the lateral surface of the patella. Attachment straps are fixed directly or otherwise operably coupled to the brace plate and may extend from the elastic sleeve at points directly above and below the patella. The straps are of a sufficient length to pass around the medial side of the knee, and across the back thereof to a point at the lateral side of the knee. The attachment straps attach at the lateral side of the knee to the upper and lower cuff members of a support brace, each cuff member including a hinging arm which extends along the lateral side of the user's knee when the cuffs are correctly positioned on the user's thigh and lower leg. The attachment straps from the support brace pass behind the user's leg and attach directly to the hinge arms thereof to secure it to the user's leg. The attachment of the brace plate straps to the cuffs of the support brace fix the brace plate in its proper position relative to the support brace and function to stabilize and apply a mechanical force to the lateral side of the patella. The support brace also includes a hinge attaching the upper and lower hinge arms together, the hinge including a locking mechanism which prevents rotation of the hinge beyond a predetermined position in order to resist hyperextension of the knee. Thus, when the knee joint is rotated, the patella is prevented from moving in a lateral direction relative to the remaining structure of the knee, thus prohibiting misplacement or subluxation thereof. If desired, the ends of the elastic sleeve may be folded over the ends of the cuffs of the supporting brace in order to aid the entire device to function as a integral unit.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Patellar stability results from dynamic (muscular), geometric (bone), and static (ligament) components acting in concert. A deficiency in any or all of these components may result in patellar instability. Consequently, effective patellar bracing should enhance and facilitate all of these components as much as possible.

Dynamic (muscular) stability is best obtained through proper neuromuscular training; however, muscular effects can be enhanced through bracing by controlling femoral-tibial flexion angles. By blocking hyperextension, the muscles are afforded a greater mechanical advantage in order to control internal tibial rotation and thus reduce rotational forces at the knee. Muscle function and patellofemoral joint reaction are also enhanced by blocking hyperextension.

Geometric or bony restraints can likewise be enhanced if hyperextension is prevented. In some cases, patellofemoral congruence can be increased with increased knee flexion (bending). Also, due to the anatomy of the knee, increasing knee flexion results in a greater surface of the patella coming into contact with the femur.

It can also help to enhance geometric (bone) restraints by controlling medial and lateral rotation of the knee joint. Increased medial rotation at the knee results in passive subluxation of the patella laterally, and increased lateral rotation results in active lateral patellar subluxation secondary to muscle contraction.

Figure 1:
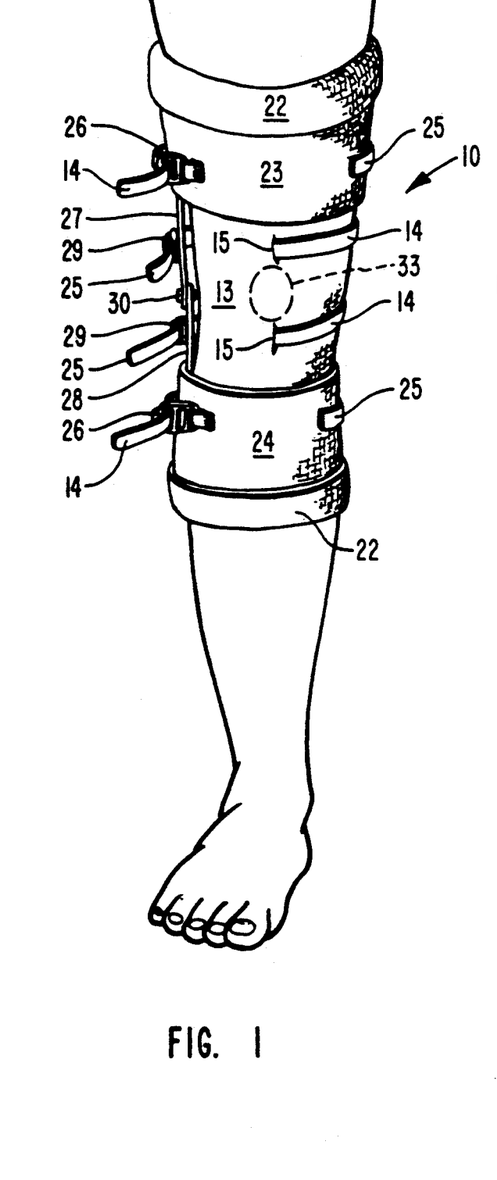
FIG. 1 is a front view of one presently preferred embodiment of a patella-femoral bracing device made in accordance with the principles of the present invention, showing the device correctly positioned and secured about a user's knee (with the patella shown in large dashed lines)

Consistent with the foregoing, one presently preferred embodiment of the patella-femoral bracing device of the present invention, designated generally at 10, is illustrated in its entirety in FIG. 1. As shown, brace 10 is positioned about the knee area of a user's leg so as to cover the entire knee joint, including the lower part of the user's thigh and the upper part of the user's lower leg. Brace 10 includes a buttressing system (see bracing plate 16 in FIG. 2(a)) to resist abnormal lateral subluxation of the patella when the knee approaches extension. Brace 10 also includes a tibial and femoral shell system (see cuffs 23 and 24) attached to a single-hinge system (see hinge arms 28 and 29) to facilitate bilateral application of the brace while also controlling medial-lateral rotation of the knee joint. The hinge system further includes a hyperextension stop (see FIGS. 7(a) and 7(b)) to block knee hyperextension, thus improving patellofemoral congruity.

It will be readily understood that the components of the present invention, as generally described and illustrated in the Figures herein, could be arranged and designed in a wide variety of different configurations. Thus, the following more detailed description of the embodiments of the present invention, as represented in FIGS. 1 through 7(b), is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 2A:
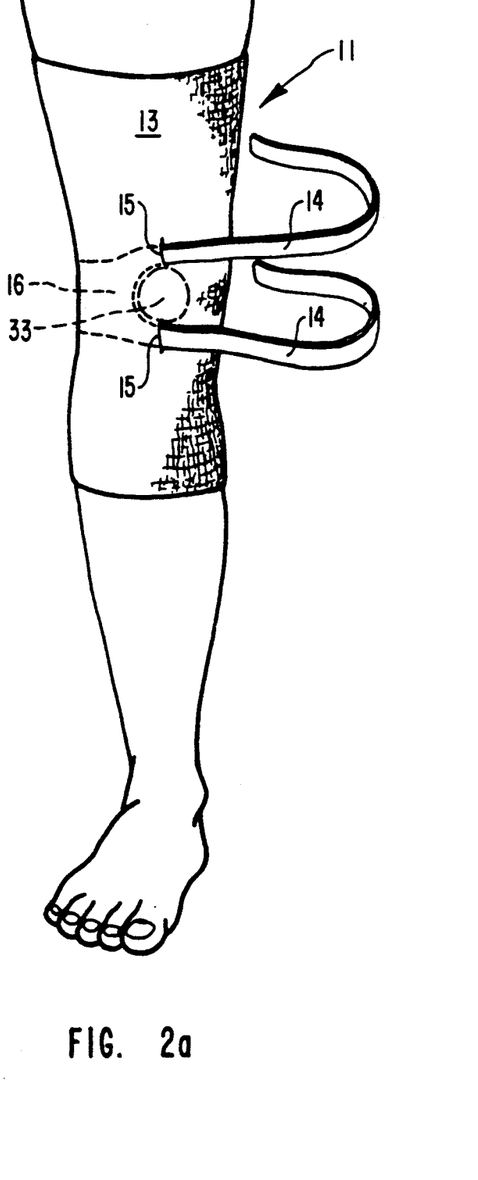
FIG. 2(a) is a front view of one presently preferred embodiment of an elastic sleeve made in accordance with the principles of the present invention, having included therein the bracing plate shown in small dashed lines (with the patella shown in large dashed lines)
Figure 2B:
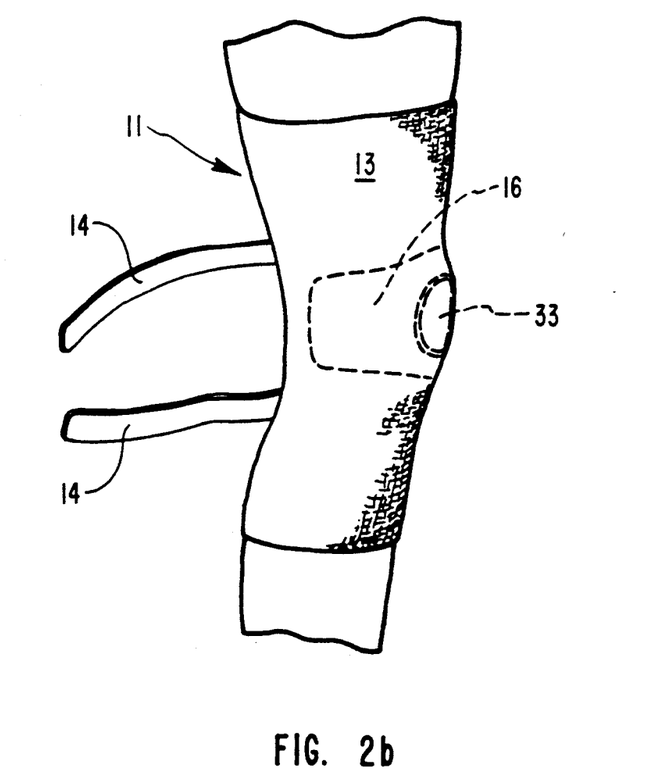
FIG. 2(b) is a side view of an elastic sleeve made in accordance with the principles of the present invention (also showing the brace plate in small dashed lines and the patella in large dashed lines)
Figure 5:
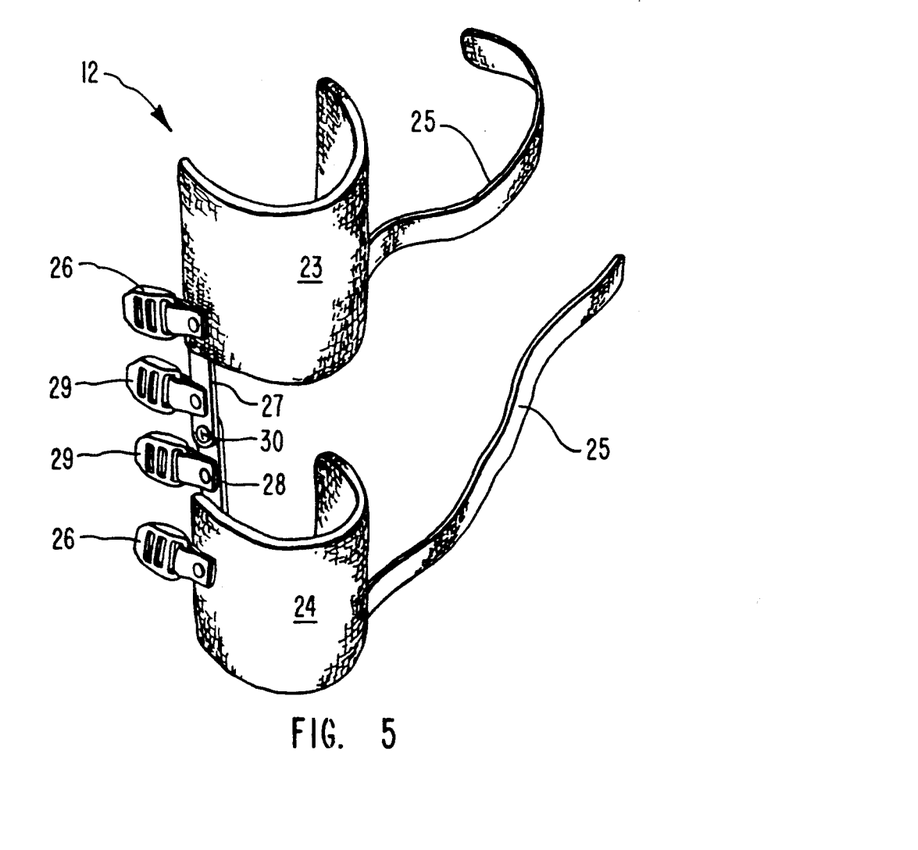
FIG. 5 is a perspective view of one presently preferred embodiment of a supporting brace formed in accordance with the principles of the present invention, which is to be located and secured about the user's leg over the elastic sleeve, and to which the straps of the brace plate are to be attached.

As shown best in FIGS. 2(a) and 2(b), device 10 includes an elastic sleeve 11 over which is mounted a supporting brace 12 (see FIG. 5). Sleeve 11 has incorporated therein a brace plate 16 which is fixed relative to the elastic sleeve 11. Brace plate 16 includes or is otherwise operably coupled to a pair of straps 14 which extend from the sleeve 11 and pass around the medial side and back of the user's leg to connect to the supporting brace 12.

As shown in FIG. 2(a), the elastic sleeve 11 is sized so as to fit snugly about the user's leg, the sleeve being sized so that the leg will cause it to stretch somewhat so that the elastic in the sleeve 11 will hold it in its proper position thereover.

The sleeve is preferably of a length sufficient to extend well up the user's thigh and well down the top portion of the user's lower leg and is preferably formed of an elasticized material which is stretchable in all directions (as opposed to many types of elasticized material which stretch in only a single direction). One example of such material is known as VITALO, which is a registered trademark of Sport-Medizin of Italy.

Figure 4:
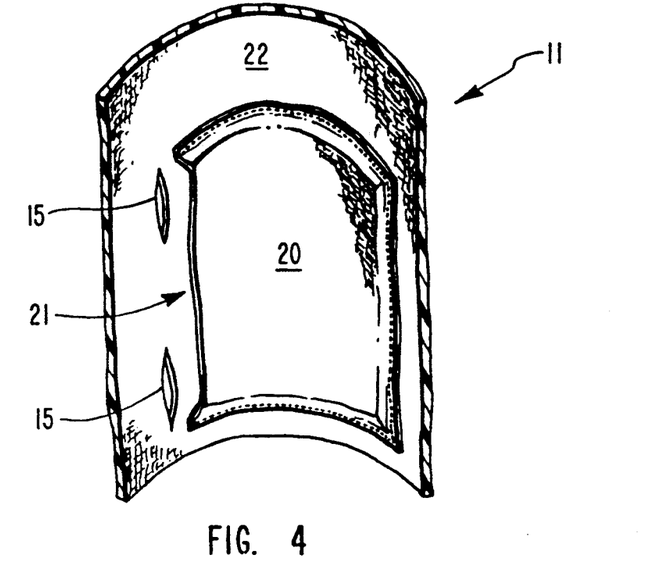
FIG. 4 is a partial perspective view of the interior surface of an elastic sleeve formed in accordance with the principles of the present invention, showing the pocket and openings used to secure the bracing plate thereto.

As best seen in FIGS. 2(a) and 4, the elastic sleeve 11 includes a pair of slit shaped openings 15 through which straps 14 of the brace plate 16 can pass. The straps 14 are of a sufficient length to pass approximately ¾ of the distance around the user's leg so as to be attachable to the supporting brace 12 in a manner explained below.

Figure 3:
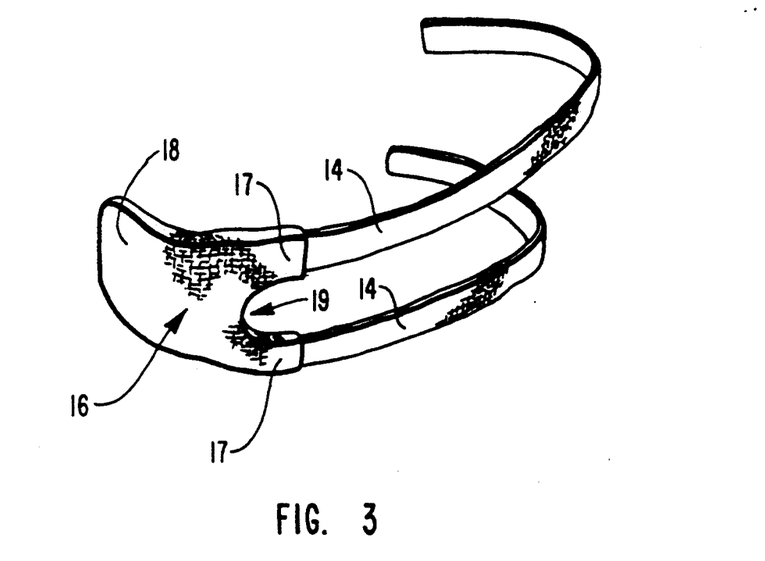
FIG. 3 is a perspective view of one presently preferred embodiment of a brace plate made in accordance with the principles of the present invention.

As shown in FIG. 3, brace plate 16 includes a pair of arms 17 which are located in generally parallel spaced apart relationship to form a generally concave patella contacting surface 19 therebetween. The brace plate 16 may optionally also include an extension 18 which extends away from the arms 17 in a generally curvilinear fashion so as to conform to the curvature of the knee joint. The extension 18 functions to protect the lateral side of the knee from injury or from incidental contact with the support brace 12. Extension 18 also functions to aid in anchoring and securing brace plate 16 in its correct position about the user's knee.

As is best shown in FIGS. 2(a) and 2(b), the brace plate 16 (shown in dashed lines) is positioned about the lateral side of the user's knee so that the concave contacting surface 19 thereof is located adjacent and somewhat conforms to the lateral side of the user's patella 33, with the extension 18 thereof extending around the lateral side of the user's knee joint. Significantly, brace plate 16 is designed and used to apply force to the lateral and slightly inferior surfaces of the patella 33 in order to assist in maintaining proper patellar position, as will be explained further below. Thus, for example, brace place 16 may be positioned on a user so as to apply a lateral force to the patella in an upward direction at an angle of approximately 30 degrees from the horizontal.

The brace plate 16 of the present invention is intended to be formed of a semi-rigid, semi-flexible material. That is, the plate 16 is intended to be sufficiently rigid to hold its form so as to be easily positioned in its correct location about the user's knee, and semi-flexible to allow it to conform to the knee's anatomy. The preferred materials used in the formation of bracing plate 16 are silicone and polyethylene. For example, bracing plate 16 may comprise a polyethylene plate covered with a soft silicone material. However, any material having similar semi-rigid, semi-flexible characteristics may be used. Materials used as the semiflexible material preferably have a Shore Durometer hardness of 15 or less as measured by ASTM Test D-2240-86.

As shown in FIG. 4, the interior surface 22 of the flexible sleeve 11 can include a pocket 20 having opening 21 therein into which the brace plate 16 may be inserted. The pocket 20 functions to hold the brace plate 16 in its correct orientation relative to the sleeve 11. The pocket 20 is most useful when the user is mounting the sleeve 11 on the leg, since it holds the brace plate 16 in its proper orientation while the sleeve 11 is being manipulated into position about the knee. Although pocket 20 is shown in the preferred embodiment as the means of holding the brace plate 16, it is anticipated that the brace plate 16 may be held in sleeve 11 in any other well known manner such as by means of adhesive, by being sewn in place, or with mechanical fasteners.

Slits 15 in sleeve 11 are centered directly above and below the patella 33 when the sleeve 11 is correctly positioned on the user's leg. The straps 14 pass through slits 15 until plate arms 17 are located approximately adjacent to the slits 15. In this position, the concave contacting surface 19 of the brace plate 16 contacts and completely surrounds a lateral side of the user's patella 33.

Once the user has positioned the sleeve 11 on the leg in the manner as shown in FIGS. 2(a) and 2(b), the supporting brace 12 is then positioned over the exterior surface 13 thereof in the manner shown in FIG. 1. The supporting brace 12 functions to provide a rigid support to which the straps 14 of the brace plate 16 can be attached as will be explained below.

As shown in FIG. 5, the supporting brace 12 includes an upper cuff 23 and a lower cuff 24 which are formed from a generally U-shaped rigid or semi-rigid material. Each cuff 23 and 24 may include padding on the interior surfaces thereof for comfort to the patient in accordance with well known cuff designs.

The use of such rigid or semi-rigid cuffs 23 and 24 significantly enhances the hyperextension stop capabilities of device 10, which will be discussed further below. Without such cuffs, any hyperextension stop capabilities would rely upon a soft tissue connection with the user's leg, rendering the hyperextension stop largely ineffectual.

It is also an important feature of the present invention that the upper and lower cuffs 23 and 24, respectively, be of a size so that they extend around a substantial portion of the user's leg. Preferably, the cuffs 23 and 24 will extend around at least 50% of the circumference of the portion of the user's leg to which they are attached. A supporting brace 12 having cuffs of this dimension can be more securely attached to the user's leg than those with smaller cuffs. Further, the larger cuffs 23 and 24 are less likely to be rotated relative to the user's leg as a result of an impact or other force incident thereon during use.

Each of upper and lower cuffs 23 and 24, respectively, includes a strap 25 for securing the supporting brace 12 to the user's leg and a buckle 26 for securing the patella brace straps 14 to the supporting brace 12. Straps 14 are thus attachable to the buckles 26 of the supporting brace 12, and are adjustable to adjust the medial pressure applied to the user's patella 33 by the brace plate 16. Although straps 14 and buckles 26 are shown in the preferred embodiment of the present invention, it is anticipated that any strap and attachment arrangement allowing for direct attachment of the brace plate 16 to the supporting brace 12, is contemplated to be within the scope of the present invention. For example, buckles 26 may be replaced with snap fasteners, VELCRO fasteners or the like. Further, if desired, straps 14 may be formed either of a non-elastic or an elastic material, depending on the particular bracing characteristics desired.

Each lateral side of the upper and lower cuffs 23 and 24 include an extension arm 27 and 28, respectively, which attach together at hinge 30. When the supporting brace 12 is correctly positioned on the user's leg, arms 27 and 28 are located on the lateral side of the user's leg such that the rotation axis of hinge 30 is located generally coaxially with the flexion/extension rotational axis of the user's knee joint, so as to be capable of tracking the hinging motion thereof. Each arm 27 and 28 has a buckle 29 included thereon which is used to secure straps 25 of the support brace plate 12.

Figure 7A:
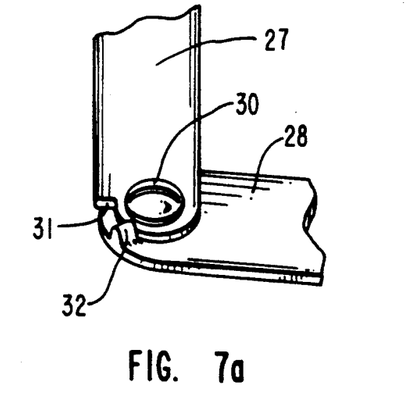
FIG. 7(a) is a partial perspective view of a hinge usable in the support brace and showing the hyperextension lock unengaged.
Figure 7B:
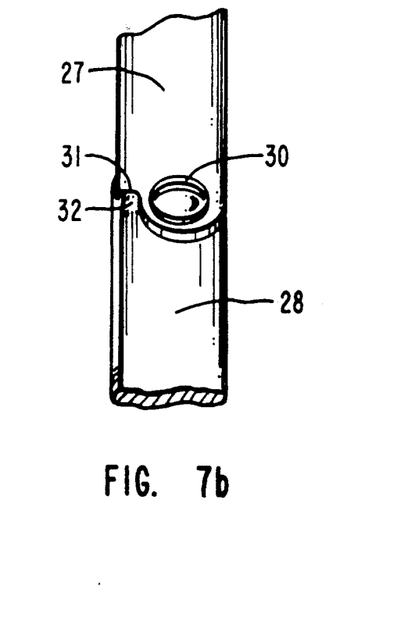
FIG. 7(b) is a partial perspective view of the hinge of FIG. 7(a) with the hyperextension lock in its engaged position.

As best shown in FIGS. 7(a) and 7(b), the hinge 30 of the support brace 12 includes a locking surface 31 on arm 27 and a locking hub 32 on arm 28. Where the hinge is in a flex position (FIG. 7a) the locking surface 31 and the locking hub 32 cannot interengage. However, as the user's knee approaches full extension (FIG. 7b), the locking hub 32 abuts with the locking surface 31 to prevent any further extension (hyperextension) thereof. This preferably occurs when the user's knee is extended at about 15 to 20 degrees.

Since the device 10 of the present invention must conform to the size of the leg of the user to which it is to be applied, it is anticipated that the various structural elements thereof be formed in a series of different sizes to accommodate different users.

Figure 8:
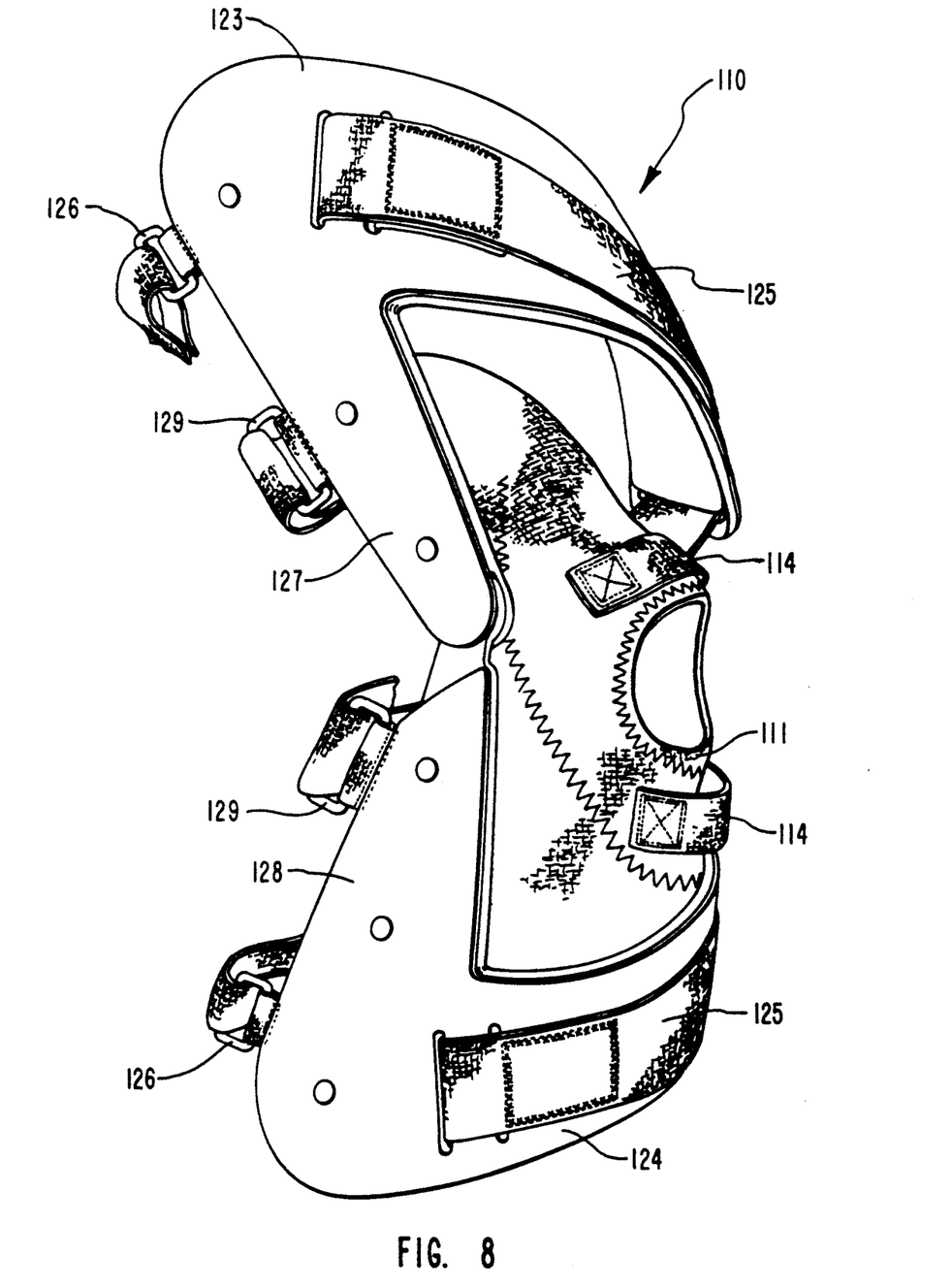
FIG. 8 is a perspective view of an alternate presently preferred embodiment of a patella-femoral bracing device made in accordance with the principles of the present invention.
Figures 9, 10:
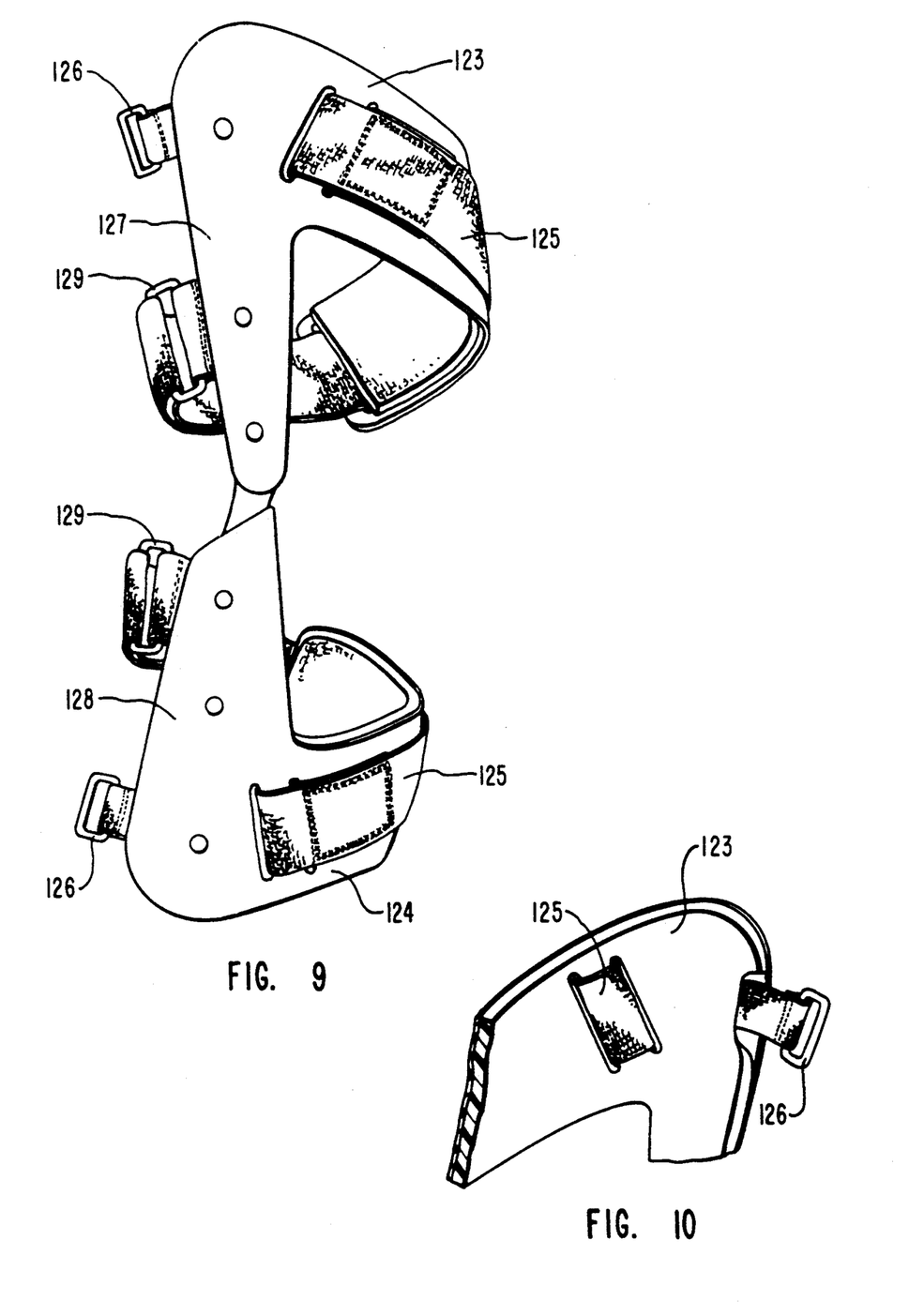
FIG. 9 is a perspective view of the supporting brace of the embodiment of FIG. 8.
FIG. 10 is a rear view, partially in section, of a portion of the upper cuff of the supporting brace of the embodiment of FIGS. 8 and 9 illustrating the alignment of the connecting straps.

An alternate embodiment 110 of the bracing device of the present invention is illustrated in FIGS. 8-10. As shown, cuffs 123 and 124 are formed so as to spiral around the user's leg when positioned as described above. Connecting straps 125 likewise spiral around the user's leg and attach to buckles 129, as shown best in FIG. 9. Straps 114 are operably coupled to the bracing plate (not shown) through sleeve 111, such as, for example, by means of sewing; and straps 114 attach to cuffs 123 and 124 by means of buckles 126. As shown best in FIG. 10, buckles 126 are preferably positioned so as to be approximately in line with the point of origin of straps 125.

As indicated above, brace plate 16 may not include a protective extension 18 (see FIG. 3). In such case, as depicted in FIGS. 8 and 9, hinge arms 127 and 128 may advantageously be coated with a suitable resilient material, such as, for example, a resilient plastic cushioning material. This resilient coating will thus protect the lateral side of a user's knee from injury or from incidental contact with the support brace.

In use, referring again to FIGS. 1 through 7(b), the upper cuff 23 is placed against surface 13 of the portion of the sleeve 11 at the front of the user's upper leg, and the strap 25 thereof is passed behind the leg and attached into buckle 29. The strap 25 is then tightened to secure the cuff 23 firmly against the thigh. Similarly, cuff 24 is placed against surface 13 of sleeve 11 so as to surround the upper shin area of the front of the user's lower leg, and the strap 25 located thereon is passed behind the user's leg and attached to buckle 29. The strap 25 is tightened to firmly secure cuff 24 to the user's upper shin area.

Figure 6:
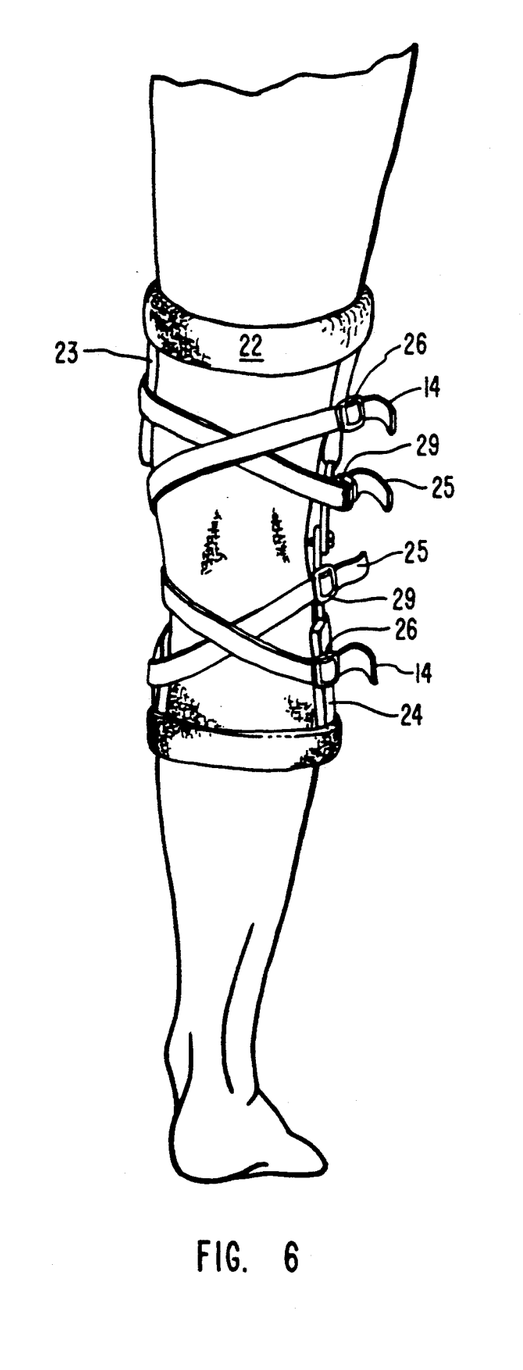
FIG. 6 is a rear view of the embodiment of the brace device illustrated in FIG. 1.

As shown in FIGS. 1 and 6, bracing plate 16 is integrated through straps 14 with the support brace 12. This positive connection through straps 14 with bracing plate 16 allows dynamic force application to the patella 33. As shown, straps 14 wrap around the medial and posterior aspects of the user's knee, and connect to the upper and lower cuffs 23 and 24 of support brace 12 such that the thigh side strap connection is superior to its origin on the bracing plate 16 and the calf side strap connection is inferior to its origin on the bracing plate 16 (see FIG. 6).

Once the supporting brace 12 is secured over the elastic sleeve 11 to the user's leg, and the straps 14 are secured to buckles 26 thereof, the device 10 of the present invention appears substantially as shown in FIGS. 1 and 6. If desired, the upper and lower ends of the elastic sleeve 11 may be pulled away from the user's leg and folded over the upper and lower portions of the upper and lower cuffs 23 and 24, as depicted at 22 in FIGS. 1 and 6. In this manner, the elasticity of the sleeve 11 tends to aid in securing the support brace 12 in its correct position relative to sleeve 11. Such integration of sleeve 11 with support brace 12 also tends to hold the device 10 together to aid in its functioning as an integral unit and in maintaining proper brace position throughout the knee's range of motion.

It is evident from the above disclosure that when the device 10 of the present invention is attached correctly to a user's leg, the user's patella 23 will be at least partially surrounded on its lateral side by the brace plate 16. Since the brace plate 16 is fixed in its lateral position by straps 14 which are directly attached to supporting brace 12 at buckles 26 (the support brace 12 itself being securely fixed in position relative to the user's leg by means of straps 25 and buckles 29, and also the folded ends 22 of sleeve 11), the user's patella 33 is prevented from moving laterally with respect to the remaining structure of the knee. The brace plate 16 can be secured by straps 14 to continuously provide a pressure in the medial direction against the side of the patella to prevent subluxation in the lateral direction. Since subluxation only occurs in the lateral direction, bracing such as described in the present invention is sufficient for its prevention.

Since straps 14 directly fix the location of the brace plate 16 relative to the arms 27 and 28 of the support brace 12, flexion/extension rotational motion of the knee has no detrimental effect on the functioning of the device 10. Regardless of the amount of flexion of the knee joint, the brace plate 16 remains correctly positioned against the lateral side of the patella 33 to hold it in its proper orientation relative to the remaining structure of the knee. Any tendency of the patella 33 to move in a lateral direction is resisted by the brace plate 16.

Significantly, as the user's knee approaches full extension, a mechanism creates a dynamic force application which helps to maintain and stabilize the patella in its correct position, thus reducing lateral subluxation and hypermobility. As the user's knee comes toward full extension, the user's thigh and calf apply pressure to the cuffs 23 and 24, and the brace device 10 becomes locked into extension due to the engagement of locking surface 31 with locking hub 32. As the brace device 10 is forced into this locked position and the user's knee tries to move into further extension, the knee begins to back out of the device 10 posteriorly. As it does so, straps 25 secure the cuffs to the user's leg, and the user's leg exerts a force on straps 14. This tightens the straps 14 and applies a dynamic mechanical force through bracing plate 16 to the lateral inferior aspect of the patella 33.

Since hyperextension of the user's knee is resisted, the user's patella 33 has no opportunity to slip below the brace plate 16. Continuous contact with and lateral pressure from brace plate 16 is therefore assured.

Referring again to FIGS. 2(a) and 2(b) and FIG. 3, the extension 18 of the brace plate 16, when properly positioned on the knee, is located between the lateral side of the user's knee and the arms 27 and 28 of the supporting brace 12. The lateral side of the knee is therefore doubly protected from injury due to impact or other forces directed at its lateral side. This double protection is a result of arms 27 and 28 being capable of absorbing lateral forces along with the extension 18 of the bracing plate 16. Arms 27 and 28 also inhibit medial-lateral rotation of the knee, thereby enhancing the knee's geometric (bone) restraints.

It is an important feature of the device 10 of the present invention to have the medial side of the user's leg be free of any hinge member or hinge arms associated therewith. This is often important in the treatment of a patient subject to patellar subluxation in that, generally, a patient with this disorder experiences the problem in both knees at the same time. In such cases, the patient must wear a device 10 on each leg (each device 10 being a mirror image of the opposite device). Using the design of the present invention, a user may easily and comfortably use a brace 10 on each leg simultaneously, without the complication of having a portion of one device 10 interfering with its counterpart on the opposite knee.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A bracing device for resisting subluxation of the patella of a user's knee, comprising:
   bracing means for location adjacent the lateral side of the patella;
   positioning means substantially encircling the user's knee and functionally cooperating with said bracing means for maintaining said bracing means in its proper position relative to the patella;
   rigid support means for restricting medial-lateral rotation of the user's knee, the rigid support means being securable to the user's leg independent of both said bracing means and said positioning means; and
   means for operably connecting said bracing means to said rigid support means so as to interactively impart a dynamic medial force to the patella as the user's leg approaches full extension, said means for operably connecting being the sole means connecting the bracing means and positioning means to said rigid support means, whereby said bracing means is fixed in its lateral orientation relative to said rigid support means by said connecting means and the patella of the user's knee is prevented from subluxation due to medial forces applied thereto as a result of the relative lateral fixation of said bracing means with respect to said rigid support means.

2. A bracing device according to claim 1 wherein said means for operably connecting said bracing means to said rigid support means includes at least one non-elastic strap.

3. A bracing device according to claim 2 wherein said connecting means includes two straps, one end of each of said straps being attached to said bracing means such that when said bracing means is correctly positioned adjacent the lateral side of the patella, one strap passes above the patella around the medial side and the back of the user's knee and attaches to said rigid support means at a location adjacent the lateral side of the user's thigh, and the other strap passes below the patella around the medial side and the back of the user's knee and attaches to the rigid support means at a location adjacent the lateral side of the user's calf.

4. A bracing device according to claim 1 wherein said bracing means has a contacting surface which is concave in shape and located directly adjacent the lateral side of the patella when in use, whereby force of said connecting means on said bracing means causes said contacting surface to apply a pressure against the lateral side of the patella in the medial direction.

5. A bracing device according to claim 1 wherein said rigid support means includes an upper cuff and a lower cuff, said upper and lower cuffs each having a hinge arm extending therefrom, said hinge arms being attached together by a hinge.

6. A bracing device according to claim 5 wherein said connecting means operably connects said bracing means to said cuffs of said rigid support means.

7. A bracing device according to claim 5 wherein said rigid support means further includes means cooperating with said hinge for preventing hyperextension of a user's knee to which said bracing device is properly attached.

8. A bracing device according to claim 1 wherein said positioning means comprises a generally cylindrical elastic sleeve having a p

* * * * *

UNITED STATES PATENT AND TRADEMARK OFFICE
CERTIFICATE OF CORRECTION

PATENT NO. : 5,277,697
DATED : January 11, 1994
INVENTOR(S) : France et al.

It is certified that error appears in the above-identified patent and that said Letters Patent is hereby corrected as shown below:

In column 10, line 67, after the words "elastic sleeve having a p"
please insert therefor -- ocket on an interior surface thereof, and said bracing means includes a bracing plate having a pair of spaced apart substantially parallel arm portions which form a generally concave contacting surface therebetween, said bracing plate being locatable in the pocket on the interior surface of said sleeve and said sleeve having a pair of openings therethrough which allow a portion of said connecting means to pass therethrough from an exterior surface thereof to attach to said arms of said bracing plate. ---

Signed and Sealed this

Twentieth Day of September, 1994

Attest:

BRUCE LEHMAN

*Attesting Officer*  *Commissioner of Patents and Trademarks*